United States Patent
Pohl

(10) Patent No.: US 9,550,804 B2
(45) Date of Patent: Jan. 24, 2017

(54) DOSAGE FORM TO INCREASE PRASTERONE BIOAVAILABILITY

(71) Applicant: J. Mark Pohl, Morristown, NJ (US)

(72) Inventor: J. Mark Pohl, Morristown, NJ (US)

(73) Assignee: Health Science Funding, LLC, Morristown, NJ (US)

( * ) Notice: Subject to any disclaimer, the term of this patent is extended or adjusted under 35 U.S.C. 154(b) by 0 days.

(21) Appl. No.: 14/450,548

(22) Filed: Aug. 4, 2014

(65) Prior Publication Data

US 2014/0343026 A1 Nov. 20, 2014

Related U.S. Application Data

(62) Division of application No. 13/453,987, filed on Apr. 23, 2012, now Pat. No. 8,900,631.

(60) Provisional application No. 61/480,404, filed on Apr. 29, 2011, provisional application No. 61/480,365, filed on Apr. 28, 2011.

(51) Int. Cl.
```
C07J 1/00       (2006.01)
A61K 31/5685    (2006.01)
A61K 9/14       (2006.01)
A61K 9/48       (2006.01)
```

(52) U.S. Cl.
CPC .............. *C07J 1/00* (2013.01); *A61K 9/145* (2013.01); *A61K 9/4858* (2013.01); *A61K 9/4891* (2013.01); *A61K 31/5685* (2013.01); *C07J 1/0011* (2013.01)

(58) Field of Classification Search
CPC .... A61K 2300/00; A61K 45/06; A61K 31/58; A61K 31/573; A61K 31/4439; A61K 31/565; A61K 9/0014; A61K 31/5685; A61K 31/122; A61K 31/192; A61K 31/202; A61K 31/519; A61K 31/568; A61K 36/185
See application file for complete search history.

(56) References Cited

U.S. PATENT DOCUMENTS

| | | | |
|---|---|---|---|
| 5,407,684 A | 4/1995 | Loria et al. | |
| 7,374,779 B2 | 5/2008 | Chen et al. | |
| 2003/0236236 A1 | 12/2003 | Chen et al. | |
| 2005/0158377 A1 | 7/2005 | Popp | |
| 2011/0020438 A1 | 1/2011 | Andrysek et al. | |

FOREIGN PATENT DOCUMENTS

| | | |
|---|---|---|
| WO | WO96/11675 A1 | 4/1996 |
| WO | WO97/40823 A1 | 11/1997 |
| WO | WO99/08666 A2 | 2/1999 |

OTHER PUBLICATIONS

Gompel, A. and Piette, J.C. "Systemic lupus erythematosus and hormone replacement therapy", Menopause International 2007, 13: 65-70. Published Jun. 2007.*
Bornstein, et al., "Plasma dihyroepiandrosterone levels during experimental endotoxemia and anti-inflammatory therapy in humans," Crit. Care Med., 2000, vol. 28, No. 6.
"Ibuprofen Dosage", Drugs.com entry. Published online Feb. 25, 2010.
"Women over 40 with High FSH" Message Board, "Jean TX: dhea Micron 5—the brand might make a difference", Sep. 27, 2007.
"Ultra Micronized DHEA (Dehydroepiandrosterone) Micron 5 DHEA", McPherson Labs sales sheet, accessed online Oct. 25, 2013.

\* cited by examiner

*Primary Examiner* — Audrea Buckley
(74) *Attorney, Agent, or Firm* — Pharmaceutical Patent Attorneys, LLC

(57) ABSTRACT

A way to formulate prasterone to both increase its oral bioavailability, and decrease the variability of its oral bioavailability.

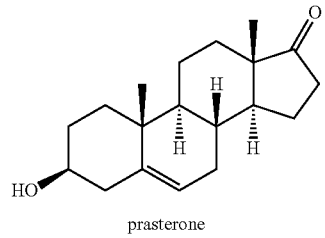

prasterone

In contrast to the approach taught by the prior art, the instant approach is amenable to scale-up to commercial scale. Further, the resulting product is amenable to analysis using standard, known quantitative analytical techniques; thus, unlike the prior art approach, the instant approach may be used to manufacture a product in conformity with applicable regulatory standards.

4 Claims, No Drawings

DOSAGE FORM TO INCREASE PRASTERONE BIOAVAILABILITY

RELATED APPLICATIONS

This application is a divisional application of U.S. application Ser. No. 13/453,987, filed on 23 Apr. 2012; which claims priority from U.S. Provisional Application Ser. No. 61/480,365 filed 28 Apr. 2011 and U.S. Provisional Application Ser. No. 61/480,404 filed 29 Apr. 2011; all of which are incorporated herein by reference in their entirety.

GOVERNMENT INTEREST

None

BACKGROUND

Prasterone has the systematic name (3S,8R,9S,10R,13S,14S)-3-hydroxy-10,13-dimethyl-3,4,7,8,9,10,11,12,13,14,15,16-dodecahydro-1H-cyclopenta[a]phenanthren-17(2H)-one. This compound has the structure shown:

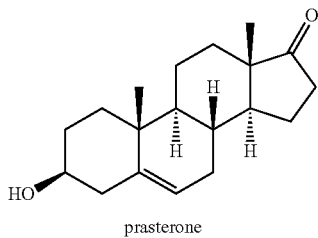

prasterone

This compound has the epiandrosterone polycyclic ring system core, and this ring system is dehydrogenated at the 5-position; thus, this compound is often called "5-dehydroepiandrosterone." It is one of perhaps twenty different species of mono-dehydrated epiandrostenedione, thus one of twenty possible "dehydroepiandrostenedione" compounds.

Prasterone is dimorphous. Both forms, however, are solid crystals at physiological temperatures (melting point 140-41° for the needle form, 152-53° for the leaflet form). Prasterone is poorly soluble in water (63.5 mg/L water). Prasterone is relatively lipophilic, having a log P (octanol-water)=3.23. Prasterone is thus known in the art as poorly bioavailable.

One solution to this problem has been to simply administer large doses. For example, Fernand LABRIE, U.S. Pat. No. 5,728,688, teaches human clinical testing of daily doses of 1.6 grams per day, see 4:66 et seq. LABRIE also teaches laboratory rat doses of 450 mg/kg, see 3:55 et seq. Given that the average American adult male weight is 86.6 kilograms, and assuming (an incorrect assumption) that there is a 1:1 correspondence between human and rat dosing, this implies a human dose of about 39 grams per day. Such large daily doses, however, may run the risk of precipitating undesired adverse side effects.

The literature is nonetheless quite sparse in teaching approaches to improve prasterone bioavailability. One approach has been to use non-oral delivery routes. For example, Fernand LABRIE, U.S. Pat. No. 5,780,460, teaches "percutaneous or transdermal administration" using a variety of "Gels, solutions, lotions, creams, ointments and transdermal patches." See e.g., Abstract; see also, e.g., Peter R. CASSON et al., *Delivery of Dehydroepiandrosterone To Premenopausal Women: Effects of Micronization and Non-Oral Administration*, 174 Amer. Journ. Obst. Gyn. 649 (1996).

Another approach, pioneered by researchers in Italy, employs alpha cyclodextrin to make a clathrate. For example, Paolo CORVI MORA et al., *Enhancement of Dehydroepiandrosterone Solubility and Bioavailability by Ternary Complexation with α-Cyclodextrin and Glycine*, 92 Journ. Pharma Sci. 2177 (2003), teaches improving the bioavailability of a type of dehydroepiandrosterone (the authors unfortunately fail to specify which of the twenty dehydroepiandrosterones they investigated) by "high-energy cogrinding with α-cyclodextrin" combined with glycine, biomaltodextrin, polyvinyl pyrrolidone and/or polyethylene glycol 400. This approach provided intriguing results. It has two critical failings, however, preventing its commercial use.

First, the method requires grinding in a laboratory-scale device: a high-energy vibrational micromill, see p. 2178. This type of apparatus is not, to my knowledge, used by any manufacturer in the world to manufacture pharmaceutical clathrates on a commercial scale. Thus, translating CORVI MORA (2003) to a commercial scale would require a significant amount of development and experimentation, apparently entailing the design and purchase of custom micromilling machinery. Further, there is no assurance that such an industrial-scale process would be ultimately successful in making a composition with improved bioavailability.

Second, CORVI MORA (2003) produces a material with a physical structure not amenable to structural analysis by known analytical methods. The resulting material, for example, appears to have no definite X-ray diffraction fingerprint. Thus, it is impossible to say whether the resulting material is in fact a clathrate, or is simply an amorphous mixture of the respective components. This inability to clearly characterize the resulting composition because given the materials used, the resulting material is likely not in fact a clathrate.

A clathrate is a complex of a "donut-shaped" cyclodextrin with a lipophilic hole region, which lipophilic hole region houses a lipophilic payload molecule. Dehydroepiandrosterones are lipophilic. Even the smallest of them, however, are simply too large to physically fit in the hydrophobic space present in α-cyclodextrin. The inability to quantitatively assay the resulting material to determine whether or not it is in fact a clathrate frustrates a potential manufacturer's ability to comply with applicable quality-control regulations. Thus, while CORVI MORA (2003) teaches a way (apparently the only way) to improve the bioavailability of an orally-administered dehydroepiandrosterone, it fails to provide the art with an industrial-scale solution.

To address these shortcomings, Paolo CORVI MORA, *Clathrates of Dehydroepiandrosterone and Corresponding Pharmaceutical Compositions*, PCT Publication WO 00/37109 (2000), teaches (at Example 11) to replace high-energy vibrational micromilling with a more conventional approach to making clathrate complexes: dissolving the dehydroepiandrosterone and alpha-cyclodextrin in a solvent to make a solution, and then removal of the solvent (by spray-drying or lyophilization). CORVI MORA (2000), however, fails to say whether this approach makes a clathrate, nor whether this approach increases or decreases dehydroepiandrosterone bioavailability.

The skilled artisan would infer that CORVI MORA (2000) does not increase dehydroepiandrosterone bioavailability, for two reasons. First, as mentioned above, even the smallest of the various dehydroepiandrosterones is simply too large to physically fit in the hydrophobic space present in alpha-cyclodextrin. Thus, the skilled artisan would expect the approach taught by CORVI MORA (2000)—dissolution and drying—to result in a simple mixture of dehydroepiandrosterone and alpha-cyclodextrin, not a clathrate complex of dehydroepiandrosterone housed within the hydrophobic region of alpha-cyclodextrin.

Second, CORVI MORA (2000) was followed three years later by CORVI MORA (2003). In the latter (2003) publication, CORVI MORA et al. (at page 2178, col. 1) note that dehydroepiandrosterone has "low and variable bioavailability." The skilled artisan would thus read CORVI MORA (2003) to teach that CORVI MORA (2000) had not solved the problem of "low and variable bioavailability."

There thus remains a need for an industrial-scale or commercial-scale way to formulate prasterone (5-dehydroepiandrosterone) to increase its bioavailability and decrease the variability of its bioavailability.

SUMMARY

The instant invention provides a way to formulate prasterone to both increase its oral bioavailability, and decrease the variability of its oral bioavailability. In contrast to the clathrate approach taught by the prior art, the instant approach is amenable to scale-up to commercial scale. Further, the resulting product is amenable to analysis using standard, known quantitative analytical techniques; thus, unlike the prior art approach, the instant approach may be used to manufacture a product in conformity with applicable regulatory standards.

BRIEF DESCRIPTION OF THE DRAWINGS

None

DETAILED DESCRIPTION

Micronization is important because it enables a higher ratio of durable liquid mass to prasterone mass. This is important to achieve the increase in bioavailability. Subsequent compression of micronized prasterone, however, will modify the particle size distribution of the micronized prasterone, making the average particle size increase. Similarly, storage over time will result in micronized particles of prasterone agglomerating into particles of larger size, thus increasing the average particle size. Thus, I believe it important to coat the micronized particles with a durable liquid vehicle. By "durable," I mean a liquid which is not entirely removed during formulation, but which remains on the micronized prasterone particles.

Suitable examples include tocopherol, fish oil, safflower oil and olive oil; I would expect each of these to inhibit particle agglomeration and thus preserve the particle size distribution of the micronized prasterone. Oils which have a relatively large proportion of polyunsaturated fatty acids or polyunsaturated fatty acid glycerides may be particularly effective. Examples of such oils include linoleic acid, linolenic acid, both of which are common components of vegetable oils. Vegetable oils which have from 50 to 90 percent (w/w) of polyunsaturated fatty acid glycerides include, for example, soyabean, corn, sunflower, safflower and linseed oils. One may also use peanut oil, albeit peanut oil has a lower total unsaturation value, and peanut antigen is associated with peanut allergy, so this type of oil, while possible, is not as preferred. Alternatively, one may use fish oil or tocopherol, for the opposite reason—in addition to serving as the durable liquid vehicle, the vehicle may confer cardiovascular benefits.

Alternatively the durable liquid vehicle could be a sterol, any of a group of naturally occurring steroid alcohols, typically derived from plants or animals. Sterols are waxy substances, insoluble in water. Note that prasterone is itself a sterol (a steroid alcohol) (years ago, prasterone was synthesized from cholesterol); thus, when I say to mix prasterone with a sterol, I intend to say to mix prasterone with a different sterol, not to mix prasterone with prasterone. Note that certain a durable liquid vehicles could result in a "eutectic" mixture, a mixture which solidifies at a lower temperature than the component durable liquid vehicle. While eutectic mixtures have their uses, they may be problematic in manufacturing soft gelatin capsules because a eutectic mixture may prove difficult to handle, requiring added heat to keep the mixture alone the eutectic temperature, so the fill material remains liquid enough to flow in the softgel encapsulation machinery.

One may use a durable liquid vehicle system made of a polar solvent (e.g., ethanol) and non-polar solvent (e.g., palm oil), together with a surfactant (e.g., a fatty acid ester) to render the polar and non-polar phases miscible. While it is possible to use a durable liquid vehicle which is lipophobic, I do not prefer it because I believe that using a relatively lipophilic vehicle will increase the bioavailability of the active ingredient viz using a relatively lipophobic vehicle.

While one should use enough of the durable liquid vehicle to inhibit particle agglomeration, the precise amount is a matter of choice; one may use just enough durable liquid vehicle to make a semi-solid paste, or enough to make a suspension or dispersion, or a solution. One could use, for example, anywhere form 1½ to 2½ milliliters of durable liquid vehicle per gram of prasterone, or about 1 liter of durable liquid vehicle for 2 kilograms of prasterone, to make an adequate amount of fill for a commercially-acceptable minimum manufacturing batch size of soft gelatin capsules of a 200 milligram dose load.

An exemplary formulation includes the following components:

|  | Amount (w/w) |
| --- | --- |
| Prasterone | 100 |
| Oleic acid | 600 |
| Ethyl alcohol | 100 |
| Lactic acid | 100 |
| Total | 900 |

The oleic acid and lactic acid are mixed at room temperature. After the mixture achieves a uniform appearance, micronized prasterone is added and stirred at 45 C until the micronized prasterone is completely wetted. Stirring continued for thirty minutes at 60 rpm. The mixture is cooled to room temperature, the ethyl alcohol is added, and the mixture stirred until no further dissolution of the prasterone is observed.

Another exemplary formulation using surfactant is as follows:

| | Amount (w/w) |
|---|---|
| Prasterone | 100 |
| Oleic acid | 600 |
| Ethyl alcohol | 50 |
| Lactic acid | 23 |
| Capmul PG-8 ™ | 252 |
| Total | 1025 |

The oleic acid and lactic acid are mixed at room temperature. After the mixture achieves a uniform appearance, micronized prasterone is added and stirred until the micronized prasterone is completely wetted. The Capmul PG-8™ is added and stirring continued at 60 rpm until the mixture is uniform and no further dissolution is observed. The ethyl alcohol is added, and the mixture stirred until no further dissolution of the prasterone is observed.

If the vehicle to prasterone ratio is too high, then the total volume of the capsule fill needed to carry a 200 milligram dose load may become too large to fit into one soft gelatin capsule. Approved sizes for soft gelatin capsules include:

| | Softgel Capsule Size | |
|---|---|---|
| | Nominal Fill Volume | |
| Size # | Minims | cm³ |
| 9.5 | 7.5-9.5 | 0.462-0.585 |
| 10 | 7.5-10.0 | 0.462-0.616 |
| 18 | 15.0-18.0 | 0.924-1.109 |
| 20 | 16.0-20.0 | 0.986-1.232 |

If the durable liquid vehicle ration is too low, the resulting capsule fill may be so thick that it becomes unwieldy or difficult to use to manufacture soft gelatin capsules.

While not absolutely necessary, one may micronize the prasterone directly in a liquid vehicle. This enables one to immediately form the vehicle-prasterone mixture into an oral dosage form. This also minimizes the potential for overheating the prasterone during a dry micronization. Alternatively, one may want to micronize under nitrogen.

The prasterone—durable liquid vehicle may be coated onto a substrate such as micronized lactose. For example, one could mix 2 parts (w/w) micronized prasterone into 1 parts (w/w) of a fatty acid such as cholesterol pivalate (trimethyl acetate) and then coat this mixture onto micronized lactose. I would expect the cholesterol pivalate to slightly increase the bioavailability (AUC) of the prasterone when compared to plain micronized prasterone coated onto lactose. Nonetheless, while the use of coated cores and the like is possible, I see no compelling advantage to using such more complex delivery systems rather than using a simple suspension of prasterone in durable liquid vehicle.

I thus intend my patent to cover, for example:

1. A soft gelatin capsule suitable for oral administration, said soft gelatin capsule comprising: a soft gelatin capsule and a fill, said fill comprising a durable liquid vehicle and at least about 100 milligrams of micronized prasterone, wherein at least about 80% of said micronized prasterone has a particle size of less than about 20 microns, said prasterone having a purity of at least about 98%, said prasterone further characterized in having no single impurity being greater than 1% (w/w) of the total mass of the prasterone, said soft gelatin capsule having an outer lubricant coating.
2. The gelatin capsule of Paragraph 1, wherein said fill is a liquid suspension or solution at normal atmospheric pressure and a temperature of about 68 F.
3. The capsule of Paragraph 1, wherein said capsule produces in a human user a serum AUC at least about 5% larger than the serum AUC, or a serum $C_{max}$ at least about 5% higher than the serum $C_{max}$, produced by the same dose of prasterone when administered as a solid compressed tablet.
4. The soft gelatin capsule of Paragraph 1, further comprising an enteric coating.
5. The soft gelatin capsule of Paragraph 1, said durable liquid vehicle selected from the group consisting of: tocopherol, fish oil, safflower oil and olive oil.
6. The soft gelatin capsule of Paragraph 1, said prasterone comprising at least about 200 mg of prasterone.
7. An oral dosage form comprising at least about 100 milligrams of micronized prasterone, said prasterone having a purity of at least about 99.5%.
8. The oral dosage form of Paragraph 7, comprising at least about 200 milligrams of prasterone.
9. The soft gelatin capsule of Paragraph 1, wherein at least about 80% of said micronized prasterone has a particle size of less than about 20 microns after six months of storage at room temperature.
10. The soft gelatin capsule of Paragraph 1, wherein at least about 99% of said micronized prasterone has a particle size of less than about 10 microns.

Given this disclosure, the skilled artisan may readily find variations of this. For example, one may use as soft gelatin capsule fill a vehicle which is free-flowing at room temperature, or one which is more viscous and perhaps even paste-like at room temperature. The choice of viscosity is one of manufacturing convenience and finished product aesthetics. Thus, I intend the legal coverage of my patent to be defined not by the specific examples recited here, but by my legal claims here appended.

I claim:
1. A method comprising:
   a. Diagnosing an adult human patient as having systemic lupus erythematosus;
   b. Administering to said human patient prasterone in an amount of at least or about 100 mg per day, for a duration effective to reduce a risk selected from: risk of breast cancer and risk of death.
2. The method of claim 1, wherein said human patient is female.
3. The method of claim 2, wherein said risk is the risk of death.
4. The method of claim 2, wherein said risk is the risk of breast cancer.

* * * * *